United States Patent [19]

Spector

[11] Patent Number: 4,781,895

[45] Date of Patent: * Nov. 1, 1988

[54] CANDLE-POWERED AROMA GENERATOR

[76] Inventor: Donald Spector, 380 Mountain Rd., Union City, N.J. 07087

[*] Notice: The portion of the term of this patent subsequent to Oct. 1, 2002 has been disclaimed.

[21] Appl. No.: 621,566

[22] Filed: Jun. 18, 1984

Related U.S. Application Data

[63] Continuation-in-part of Ser. No. 477,353, Mar. 21, 1983, Pat. No. 4,556,539, which is a continuation-in-part of Ser. No. 412,080, Aug. 27, 1982, Pat. No. 4,695,434.

[51] Int. Cl.⁴ .............................................. A61L 9/02
[52] U.S. Cl. ...................................... 422/125; 422/4; 422/5; 422/306
[58] Field of Search ....................... 422/4, 5, 125, 306; 239/53–57

[56] References Cited

U.S. PATENT DOCUMENTS

| | | | |
|---|---|---|---|
| 1,086,705 | 2/1914 | Havener | 239/55 |
| 1,535,486 | 4/1925 | Lundy | 422/125 X |
| 1,547,160 | 7/1925 | Bailey | 422/125 X |
| 1,577,604 | 3/1926 | Bauer | 422/125 |
| 2,143,246 | 1/1939 | McGray | 422/5 X |
| 2,535,802 | 12/1950 | Libson | 422/125 |
| 2,564,860 | 8/1951 | Ryberg | 239/54 |
| 2,757,278 | 7/1956 | Cloud | 422/125 X |
| 4,277,024 | 7/1981 | Spector | 239/56 X |
| 4,303,617 | 12/1981 | Bryson | 422/5 X |
| 4,306,892 | 12/1981 | Atalla et al. | 422/5 X |
| 4,346,059 | 8/1982 | Spector | 422/125 |
| 4,544,592 | 10/1985 | Spector | 239/56 X |

FOREIGN PATENT DOCUMENTS 2294717   8/1976   France ............................. 422/125

OTHER PUBLICATIONS

"Unit Operations of Chemical Engineering"; McCabe and Smith; McGraw-Hill Book Co.; 1976; p. 413–416.

*Primary Examiner*—Benoît Castel
*Attorney, Agent, or Firm*—Michael Ebert

[57] ABSTRACT

A candle-powered aroma generator in a lantern format housing a candle holder within a cylindrical container provided with a translucent shell mounted on a base and having a removable cover thereover whose roof has a central well. Below the bottom of the well is the burning wick of a candle supported in the holder, the candle flame heating the bottom which then functions as a miniature hot plate. Received in the well and resting on the hot plate is a replaceable aroma cartridge within whose cavity is a porous pad that partitions the cavity into upper and lower air chambers. The lower chamber is in heat transfer relation to the hot plate and the upper chamber has a vent therein. The pad is impregnated with a volatile liquid fragrance, and the heated air in the lower chamber produces a positive pressure therein which forces the air through the pad to volatilize the fragrance. The resultant vapor is discharged into the atmosphere through the vent.

4 Claims, 1 Drawing Sheet

CANDLE-POWERED AROMA GENERATOR

RELATED APPLICATIONS

This application is a continuation-in-part of my co-pending application Ser. No. 477,353, filed Mar. 21, 1983, now U.S. Pat. No. 4,556,539, which in turn is a continuation-in-part of an earlier application Ser. No. 412,080, filed Aug. 27, 1982, now U.S. Pat. No. 4,695,434.

BACKGROUND OF INVENTION

Field of Invention

This invention relates generally to aroma-generating devices, and more particularly to a candle-powered aroma generator in a lantern format using a scentless candle, yet providing a choice of scents.

The history of the candle goes back to the middle ages when candles were made by hand. Most modern candles are machine fabricated by a molding process which forms a cylindrical mass of tallow or wax having embedded therein a twisted linen or cotton wick that burns to emit light.

The candle continues to play a symbolic role in literature, art and religion where the candle is often used to represent joy or reverence for the divine. And because the candle spends itself, it also serves to symbolize sacrifice. Though the candle is a notoriously weak source of light, where a romantic or glamorous setting is called for, as in a posh restaurant or at a dinner party, candlelight is preferred over electric lights or other more brilliant modern types of illumination.

To enhance the romantic appeal of candlelight, it is known to use scented candles which exude a pleasing fragrance as the candle burns. There are, however, a number of drawbacks with conventional scented candles in which the perfume oil is dispersed in the wax. There is a loss of perfume after prolonged storage; hence the scent, when the candle is burned, may be very faint. Moreover, the choice of scents is quite limited, for one needs for each distinctive scent a separate candle dedicated thereto.

Chemists have succeeded in analyzing the essential oils from which natural perfumes are made, and in creating thousands of synthetic fragrances, some simulating natural products and others yielding altogether new scents. While there is an enormous range of available fragrances, including the basic fruit and floral scents and various blends of natural and synthetic fragrances, one cannot as a practical matter produce scented candles in more than a few of the more popular and commonplace scents. A consumer, therefore, wishing to create a romantic aura by means of scented candles has a very limited selection of candles to choose from.

Thus, if for a Christmas party one wishes to produce the aroma of a burning log fire, there is no scented candle which exudes this special odor.

SUMMARY OF INVENTION

In view of the foregoing, the main object of this invention is to provide a candle-powered aroma generator in a lantern format which uses a scentless candle to create various aromas.

A significant feature of the invention is that the aroma is produced by a replaceable cartridge heated by the scentless candle, the cartridge being capable of producing any known scent depending on the liquid fragrance entrapped therein. Thus the user has available a large selection of different scents to choose from.

More particularly, an object of this invention is to provide an aroma generator in the form of a lantern which protectively houses the candle and serves both as a source of illumination and scent.

Briefly stated, these objects are attained by a candle-powered aroma generator in a lantern format housing a candle holder within a cylindrical container provided with a translucent shell mounted on a base and having a removable cover thereover whose roof has a central well. Below the bottom of the well is the burning wick of a candle supported in the holder, the candle flame heating the bottom which then functions as a miniature hot plate. Received in the well and resting on the hot plate is a replaceable aroma cartridge within whose cavity is a porous pad that partitions the cavity into upper and lower air chambers. The lower chamber is in heat transfer relation to the hot plate and the upper chamber has a vent therein. The pad is impregnated with a volatile liquid fragrance, and the heated air in the lower chamber produces a positive pressure therein which forces the air through the pad to volatilize the fragrance. The resultant vapor is discharged into the atmosphere through the vent.

OUTLINE OF DRAWINGS

For a better understanding of the invention as well as other objects and further features thereof, reference is made to the following detailed description to be read in conjunction with the accompanying drawings wherein.

DESCRIPTION OF INVENTION

Figure 1:
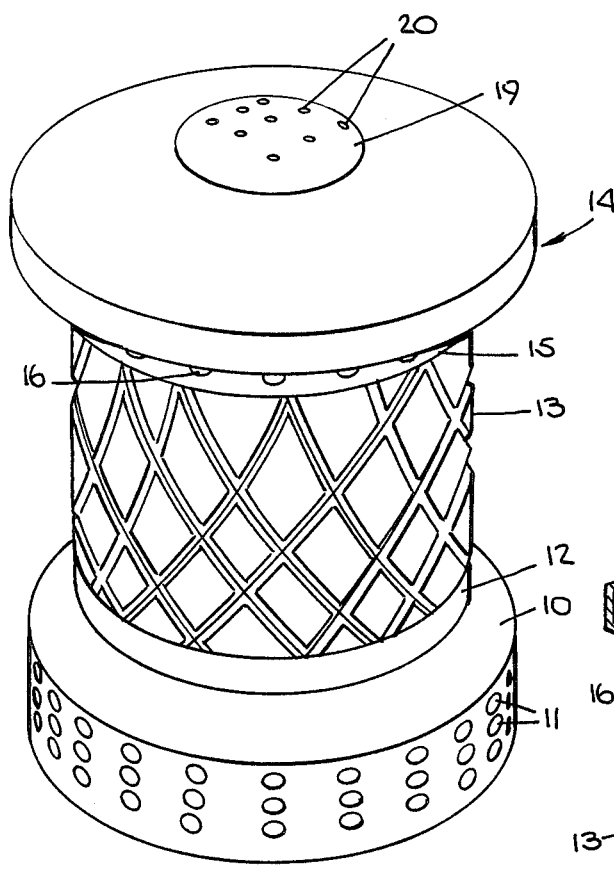
FIG. 1 is a perspective view of an aroma generator in a lantern format in accordance with the invention.
Figure 2:
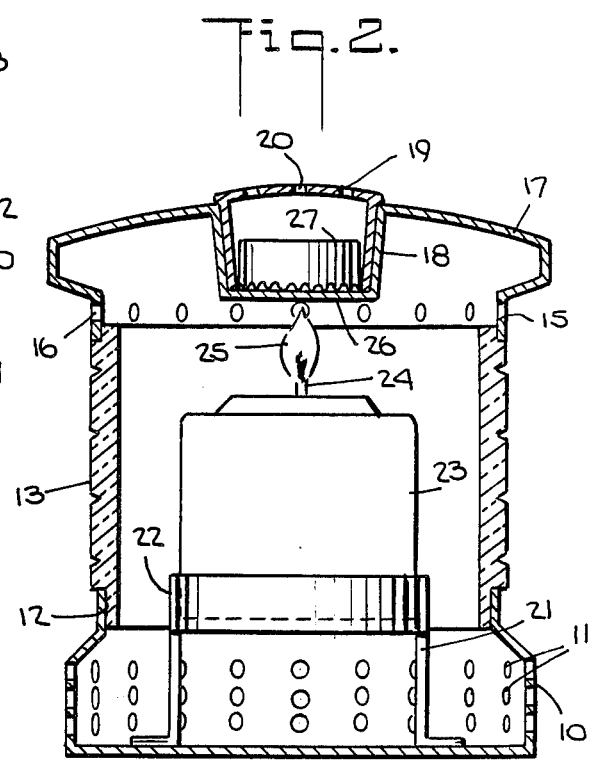
FIG. 2 is a section taken through the lantern.

Referring now to FIGS. 1 and 2, an aroma generator in a lantern format in accordance with the invention includes a cylindrical hollow base 10 having a circumferential array of vent holes 11 therein, the open top of the base having a circular rim 12.

Seated on rim 12 of the base is a cylindrical shell 13 of translucent glass or synthetic plastic material such as acrylic whose surface may be incised to form a decorative pattern. Supported on the upper end of shell 13 is a removable metal cover 14 having a circular lower apron 15. This apron is received in an annular shoulder formed on the upper end of shell 13, the apron having a circumferential series of vent holes 16 therein.

Apron 15 of cover 14 is joined to a dome-like roof 17 whose central zone is depressed to define a circular well 18. Fitting into this well is a removable cap 19 whose roof is provided with an array of vent holes 20.

Mounted on the floor of base 10 are the feet of a candle holder 21 whose raised cylindrical cup 22 is coaxial with cylindrical shell 13. Seated in cup 22 is a standard scentless candle 23 having about the same diameter as the cup. The candle has a wick 24 which burns to produce a candle flame 25.

Candle flame 25, when the candle is fresh, is just below the bottom of well 18 which then functions as a miniature hot plate 26; and as the candle proceeds to burn and consume wax, the flame position descends, but the rising heat therefrom continues to heat the hot plate.

Figure 3:
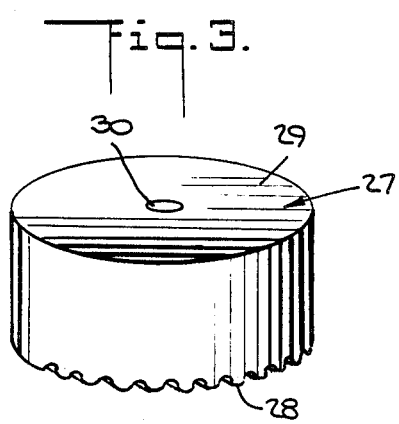
FIG. 3 is a perspective view of an aroma cartridge usable with the lantern.
Figure 4:
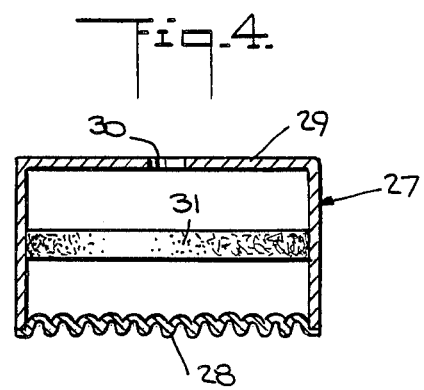
FIG. 4 is a section taken through the cartridge.

Nested in the well is a replaceable aroma cartridge 27. As shown in FIGS. 3 and 4, this cartridge is constituted by a cylindrical drum or wafer formed of metal foil or other suitable material of good heating conductivity, whose base 28 is preferably corrugated to enlarge its effective heat transfer area. The top wall 29 of the cartridge is provided with a center vent hole 30.

The internal cavity of the cartridge is partitioned by a disc-shaped pad 31 formed of porous material such as blotting paper, open-cell foam plastic or non-woven fabric, into a lower air chamber 32 and an upper air chamber 33.

Pad 31 is impregnated with a volatilize liquid fragrance and may have a fruit scent, a flower scent or any other natural or synthetic scent. Thus one may provide aroma cartridges in a great variety of fragrances so that the user can select therefrom whichever fragrance is appropriate to a given occasion. The invention is not limited to pleasing scents, and includes liquids functioning as deodorizers or as insect repellents.

When a selected cartridge 27 is nested in well 18 and the cap 19 is seated therein to conceal the cartridge, heat from the hot plate 26 is transferred into the lower air chamber 32 of the cartridge. Since the air in the chamber is confined by the pad 31 and it expands when heated, the resultant positive pressure causes hot air from the lower chamber to force its way through the porous pad to volantilize the liquid fragrance and produce a scented vapor, this vapor is discharged into the atmosphere through vent hole 30 in the cartridge.

Because there are vent holes 11 in the base of the container and vent holes 16 in the cover thereof, the container acts as a chimney to create a continuous upward flow of air which promotes burning of the candle. Thus the lantern not only protects the candle, but it also provides pleasing candlelight and at the same time exudes a pleasing aroma.

Cartridge 27 may be provided with a removable sticker to seal vent hole 30 when the cartridge is being stored so that it has a long storage life. In practice, the consumer may be provided with a large pack of miniature cartridges, each having a different scent. In this way the consumer may select any desired scent; and when a cartridge is exhausted, the consumer may replace the dead cartridge with a fresh cartridge. Because cover 14 is removable, when the candle is spent it may be replaced.

While there has been shown and described a preferred embodiment of CANDLE-POWERED AROMA GENERATOR, it will be appreciated that many changes and modifications may be made therein without, however, departing from the essential spirit thereof. Thus instead of placing the cartridge in the hot plate of a candle-powered lantern, it may be placed on other forms of hot plates, even those electrically energized. And instead of a wax candle, one may use a liquid oil candle floating in a glass of water. Also, the cartridges may be in tab form of a perforated sheet containing an array of tabs, making it possible to tear off a tab from the sheet. Also, should one run out of cartridges, one can pour perfume into the well to form a pool thereof which is volatilized by the hot plate.

I claim:

1. A candle-powered aroma generator in a lantern format comprising:
   (a) a container housing a candle holder and provided with a removable metal cover having a depressed well therein which is positioned above the flame of a candle supported in said holder whereby the bottom of the well functions as a miniature hot plate; and
   (B) a replaceable aroma cartridge receivable in said well, said cartridge being formed with a metal base of good heat conductivity and a vented top wall, said cartridge having a cavity therein partitioned by a porous pad into a vented upper chamber and in an unvented lower air chamber, the metal base of the lower air chamber resting on said bottom of the well which functions as a hot plate and being in heat exchange relation with said hot plate, said pad being impregnated with a volatile liquid fragrance whereby air heated and expanded in the lower chamber produces a positive pressure which forces the hot air through the pad to volatilize the fragrance to produce a vapor in the upper chamber which is discharged into the atmosphere through the vent in the top wall of the upper chamber.

2. A generator as set forth in claim 1, wherein said container has a translucent shell surrounding said candle.

3. A generator as set forth in claim 1, further including a vented cap receivable in said well to conceal said cartridge.

4. A generator as set forth in claim 1 wherein said cartridge base is formed of corrugated metal foil.

* * * * *